United States Patent [19]

Reich et al.

[11] 4,135,253
[45] Jan. 23, 1979

[54] CENTRIFUGAL BLOOD PUMP FOR CARDIAC ASSIST

[75] Inventors: Sanford Reich, St. Louis Park; William H. Gates, Fridley, both of Minn.

[73] Assignee: Medtronic, Inc., Minneapolis, Minn.

[21] Appl. No.: 746,008

[22] Filed: Nov. 30, 1976

[51] Int. Cl.² ............................ A61F 1/24; A61M 1/03
[52] U.S. Cl. .......................................... 3/1.7; 128/1 D; 417/420; 415/112; 415/212 R; 415/215; 415/DIG. 4
[58] Field of Search ......... 3/1.7, 1; 128/1 D, DIG. 3; 417/420; 415/DIG. 4, 112, 212 R, 215, 206

[56] References Cited

U.S. PATENT DOCUMENTS

| 3,169,486 | 2/1965 | Freed | 415/215 X |
| 3,608,088 | 9/1971 | Dorman et al. | 3/1.7 |
| 3,864,055 | 2/1975 | Kletschka et al. | 415/215 X |

OTHER PUBLICATIONS

"Prolonged Pulsatile and Nonpulsatile LV Bypass with a Centrifugal Pump" by G. G. Johnston et al, Transactions American Society for Artificial Internal Organs, vol. XXII, April 1-3, 1976, pp. 323-331.
"A Compact Low Hemolysis, Non-Thrombogenic System for Non-Thoracotomy Prolonged Left Ventricular Bypass" by E. F. Bernstein et al, Transactions ASAIO, vol. XX, 1974, pp. 643-654.
"An Artifical Heart That Doesn't Beat" AMA, Feb. 18, 1974, vol. 227, No. 7, pp. 735 and 738.

Primary Examiner—Ronald L. Frinks
Attorney, Agent, or Firm—Cameron, Kerkam, Sutton, Stowell & Stowell

[57] ABSTRACT

A centrifugal blood pump and method of pumping blood is disclosed to provide assistance for a dysfunctional heart. The pump is provided with a magnetic drive system which permits a synchronous magnetic coupling with a separate power unit disposed immediately adjacent the pump housing. The pump has a single moving part which includes the combination of an impeller connected to a magnetic drive rotor. The impeller is of improved blade and hub design to automatically move blood, and minimize formation of blood clots and fibrous amalgamation in the region of blood flow. Further, the impeller blades are configured to extend almost completely across the bottom surface of the impeller hub to enhance efficiency and clot-free operation. The magnetic drive system floats on a fluid surface of saline solution, which hydrodynamically supports and lubricates the magnetic drive rotor contained in a compartment separate from the impeller and facilitates a prolonged period of service-free operation.

17 Claims, 5 Drawing Figures

CENTRIFUGAL BLOOD PUMP FOR CARDIAC ASSIST

BACKGROND OF THE INVENTION

The present invention is directed to a centrifugal, magnetically driven blood pump to be used as a cardiac assist device, and the method of using the same. Although the primary purpose of the pump of the present invention is to provide assistance to or a replacement for a dysfunctional heart in a living body, it is presently capable to be used as a blood pump for open-heart surgery where bypass of the heart is needed or for assistance of the damaged left ventricle. In an illustrative embodiment of this invention, the blood pump may be implanted with no wire or tubes through the skin of a human, whereby a magnetic drive system is utilized which is operated from a magnetic or electromagnetic energy source outside of the body.

Modern medical practices have advanced in the field of cardiac assist devices from the early days of pacemakers to the use of cardiac assist pumps which now perform all or part of the work normally done by a failing heart. Many experimental cardiac assist pumps, in the past, have been totally implanted actuators with their own power sources or implanted devices with wires or tubes passing through the user's skin to an outside power source. There is a prior art heart pump which requires no implanted power source or wires or tubes connected to the outside power source. This pump and power source includes an impeller connected to a rotor for centrifugally pumping blood to the heart. A high-energy bar magnet is set in and secured to a transverse slot in the rotor for rotating the impeller when acted upon by an outside power source. The rotor of the pump is driven by a high-energy drive magnet similar to the bar magnet of the pump rotor connected to a power supply, such as a portable battery pack. The drive manget is intended to be disposed immediately adjacent the skin surface of the user in axial alignment with the pump rotor. Lubrication of the rotating rotor-impeller combination is done by circulating blood between the stationary parts of the pump and the rotating rotor-impeller.

With this implantable blood pump, there is a tendency for blood clots to form in the space formed between the impeller and an inclined wall of a thrust plate, disposed adjacent to the impeller. The impeller has blades which radiate from a hub in a manner as to leave a relatively large hub surface area adjacent to the thrust plate. The blood also lubricates the rotating pump parts and therefore floods in the space between the hub and thrust plate. As a result of this pump construction, the flow of blood between the large hub surface area adjacent to the thrust blade tends to be very slow thereby enhancing formation of blood clots. As a direct result of te clot formations between the impeller and the thrust plate, the impeller is forced away from the thrust plate, drawing the magnetic rotor up against the flat, rear face of the thrust plate, resulting in seizure of the pump. The present invention is an improvement over this blood pump and is designed to minimize the problem of clot formation.

SUMMARY OF THE INVENTION

It is an object of this invention to provide a centrifugal blood pump of improved design which substantially reduces the possibility of stable clot formation.

It is still another object of this invention to provide a centrifugal blood pump which is lubricated with a saline solution contained in its impeller rotor chamber.

It is a further object of this invention to provide a centrifugal blood pump wherein there is provided a seal for maintaining its rotor chamber free of blood.

In accorddance with these and other objects, there is provided a new and improved centrifugal blood pump which includes a housing divided by a baffle plate to provide an impeller chamber and a rotor chamber. An improved impeller, which substantially eliminates blood clot formation between the impeller and the baffle plate is disposed within the impeller chamber, and includes a hub having a shank receiving end and a plurality of blades which extend a sufficient distance across the shank receiving end to move blood rapidly from a space between the impeller and the baffle plate, thereby minimizing blood clot formation, and cleaning away any clots from between the impeller and the baffle plate. The rotor chamber contains a magnetic rotor which floats on a solution of saline for lubricating purposes. The baffle plate separating the two chambers includes a rotor shank seal which retains a saline solution in the rotor chamber. In addition, the saline solution is circulated periodically in the rotor chamber to flush the chamber and to replenish the saline with fresh solution. The saline solution also serves to keep blood from entering the rotor chamber from between the impeller and the rotor shank seal.

DESCRIPTION OF THE DRAWINGS

Other objects and advantages of this invention will become apparent from the following detailed description thereof and the accompanying drawings, wherein.

DETAILED DESCRIPTION OF THE PREFERRED EMBODIMENT

Figure 1:
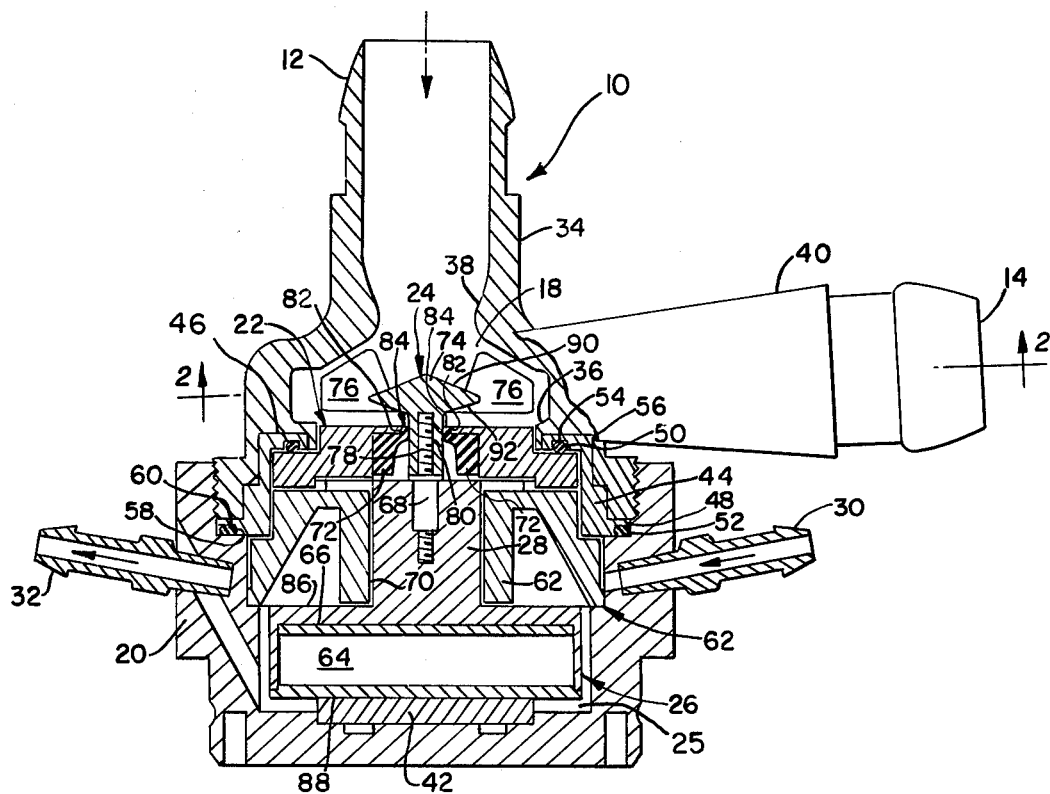
FIG. 1 is a sectioned view passing through the longitudinal axis of an improved blood pump in accordance with teachings of this invention.

Referring now to the drawings and in particular FIG. 1, the pump according to the present invention includes a cylindrical heart pump housing indicated generally at 10, having a blood inlet 12 and outlet 14. Within the pump housing 10 there is a scroll pump chamber 18 separated from a rotor housing 20 by a baffle plate 22. In the scroll pump chamber there is a blood circulating impeller 24 which forms a significant aspect of this invention and will be discussed in detail later. The rotor housing 20 contains a rotor chamber 25 and a magnetic rotor 26 and a shank 28 for connection to the impeller 24. Lubrication of the rotor 26 is done by pumping a saline solution through an inlet port 30 through the rotor housing 20 and out through outlet port 32. The cylindrical pump housing 10, includes a cylindrical scroll pump casing 34 with a transverse circular flange 36 extending inwardly from the inside surface of the pump casing 34 intermediate of the ends of the pump housing 10. The inlet opening 12 is coaxial with the longitudinal axis of the pump housing 10 and communicates through a slightly restricted orifice 38 with the scroll impeller chamber 18 from which a diffuser tube 40 is disposed tangentially with respect to the chamber 18 and down stream of the inlet opening 12, to provide discharge outlet 14.

The outside wall of pump casing 34 on the opposite side of flange 36 is threaded to receive an internally threaded rotor housing 20. Rotor housing 20 generally is of a cylindrical shape, with a sealed, closed end. A rear thrust plate 42 is disposed between the inside bottom surface of the rotor housing 20 and rotor 26. The baffle plate 22 is disposed in the opening betwen a rotor chamber 25 formed within the rotor housing 20 and the scroll chamber 18, with the baffle plate 22 pressed in sealing contact against an inner surface of an annularly shaped insert 44. The insert 44 held in place between the pump casing 34 and the rotor housing 20, extends from an annular groove 46 within the flange 36 of the casing 34 to a slot 48 formed between pump casing 34 and the rotor housing 20. A pair of O-rings 50 and 52, respectively, are disposed between an annularly shaped groove 54 with a flange portion 56 of the insert 44 and an abutting portion of the baffle plate, and a circular groove 58 within an extended portion 60 of the insert 44 and an abutting surface of the rotor housing 20 whereby the pump chamber 18 is liquid sealed with respect to the interior of the rotor housing 20. The rotor 26 is supported between the thrust plate 42 and the baffle plate 22, using a space element 62 to limit the axial movement of the rotor 26.

Rotor 26 includes a high-energy magnet 64 set in and secured in a transverse slot 66 in the rear face of the rotor 26 to form a flush fit and uninterrupted surface. The rotor 26 has a shank 28 which connects to a double ended threaded connector 68, which also connects to the impeller 24 as will be explained. There is an axially disposed opening 70 in spacer element 62 to align the shank 28 with a seal 72 in baffle plate 22.

The impeller 24 includes a generally conical hub 74 supporting a plurality of radially-extending blades 76. The impeller blades 76 are generally in the form of trapezoids secured at one end to hub 74. Hub 74 has a threaded shank 78 which is received on the connector 68. The threads of the shank 78 are opposite in direction from the direction of rotation of the rotor 26 such that accidental detachment of the impeller 24 from the rotor 26 by unscrewing the shank 78 is avoided. The shank 78 extends through an axially disposed opening 80 in the seal element 72. The seal element 72 is mounted in an axially disposed opening 82 of baffle plate 22 such that a lip 84 contacts the shank 78 to prevent blood from seeping between the shank 78 and seal element 72. The seal is positioned in the baffle plate 22 such that lip 84 is flush with the blood chamber side of baffle plate 22 to prevent any build-up of blood around the seal; this also minimizes the area of blood-seal contact and eliminates a region of potential stasis.

Figure 2:
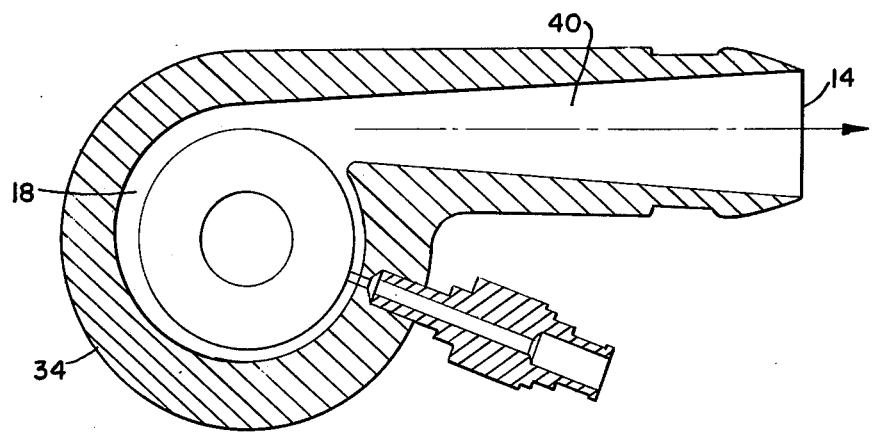
FIG. 2 is a transverse sectioned view along the line 2—2 of the heart pump in FIG. 1 and in the direction of the arrows.

Lubrication of the parallel flat surfaces 86 and 88 of the rotor 26 is accomplished by introducing a saline solution into the rotor chamber 25 through inlet port 30, shown in FIGS. 1 and 2. The saline solution circulating through rotor chamber 25 function like a fluid lubricant eliminating any friction between the moving and non-moving parts. In other words, flat surfaces 86 and 88 of rotor 26 do not come in contact with thrust plate 42 or spacer element 62 but instead rides on a fluid cushion of saline solution. The saline solution circulating throughout chamber 25 also comes in contact with seal 72 and baffle plate 22. The pressure of the saline solution against seal 72 and shank 78 of impeller 24 prevents blood from seeping from the pump chamber 18 into rotor chamber 25. The saline solution in addition to not allowing blood to pass between the seal 72 in shank 78, may cause a reverse flow of saline solution into pump chamber 18, which is harmless. The saline solution exits the rotor chamber 25 through outlet 32. The use of a saline solution to lubricate the rotor 26 has the advantage of preventing any blood which may seep into rotor chamber 25 from clotting and further it has been found that the use of saline solutions do not have a detrimental effect on the working parts of the rotor. In an illustrative embodiment of this invention, the saline solution was pumped through chamber 25 to establish pressure of 200 mm of Hg therein, whereby, as tests have indicated, that a loss of less than 20 milliliters of the saline solution was lost about the seal 72 in 24 hours of continuous pump use.

The pump 10 is constructed of materials which are compatible with body fluids with which they come into contact. For example, the pump casing 34 and rotor housing 20 are made of seamless epoxy resin coated with an elastomer, such as silicone polyurethane block copolymer. The other surfaces, with which blood comes into contact, which includes impeller 24 and baffle plate 22, may consist of pyrolytic carbon. The rotor 26 and rotor housing 20 may be made of stainless steel. The magnet 64 is formed of high-energy samarium cobalt.

Figure 3:
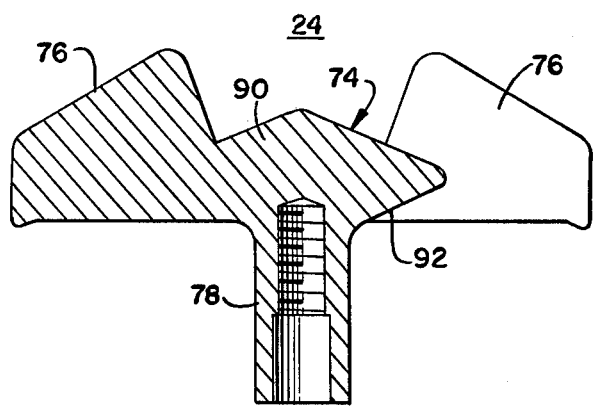
FIG. 3 is a transverse section along the line 3—3 of the impeller of FIGS. 5 and 4 and in the direction of the arrows.
Figure 4:
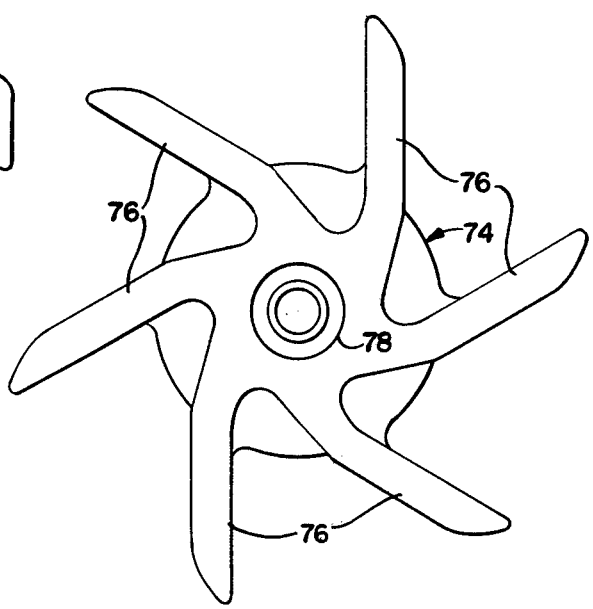
FIG. 4 is a bottom plan view of the improved impeller of the present invention, as incorporated into the blood pump of FIG. 1.
Figure 5:
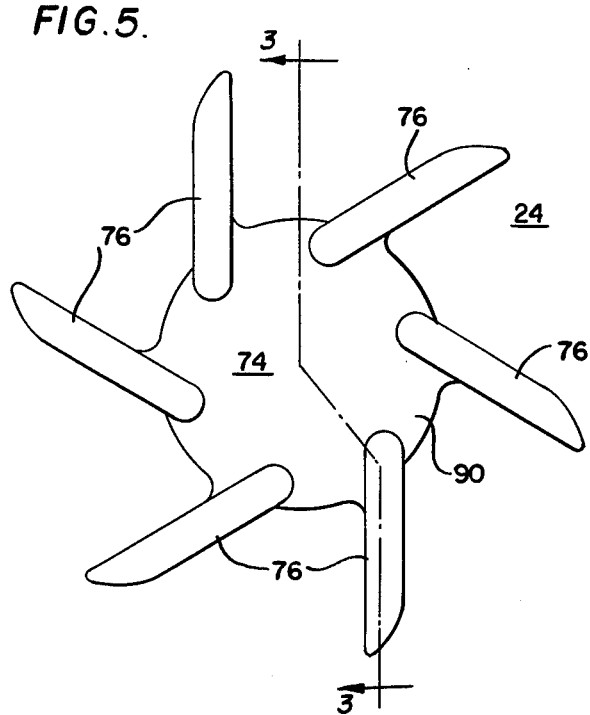
FIG. 5 is a top plan view of the improved impeller of the present invention.

Referring to FIGS. 3, 4 and 5, there is shown a cross-section view of the improved impeller 24 of this invention. The impeller hub 74 is generally a disc-shaped structure with conical end 90 and a shank end 92. The shank 78 extends transversely from the shank receiving end 92 of the hub 74. The radiating blades 76, best shown in FIGS. 3 and 4, are secured to the hub 74 such that the shank 78 extending from the hub 74 and where the blades 76 radiate from the hub 74, intersect. It is important that the baldes 76 extend across the shank receiving end 92 of the hub 74 and contact or come fairly close to contacting the shank 78 to rapidly move the blood from between the impeller hub 74 and baffle plate 22, thereby minimizing the formation of blood clots and stable fibrous deposits.

The impeller blades 76 as shown in FIG. 3 do not radiate from the center of the hub 74 but instead are off-set to the side of shank 78 and are disposed substantially tangential to the hub 74. In addition the blades 76 have a slight curvature such that the blood is contained between the blades 76 and is more efficiently pumped to outlet 14. Because of the blades 76 being off-set from the center of the hub 74 and the slight curvature of the blades 76, the blood is moved more rapidly; this desired action is also aided by the fact that the blades 76 extend far enough across the bottom surface of the hub 74 to eliminate any flat surfaces on the hub thereby minimizing regions of stasis. If impeller hub 52 had a flat surface between the hub and the baffle plate 22 there would not be sufficient pumping action of the blood and, therefore, the flow of blood would slow to a point where blood clots could form.

Figure 6:
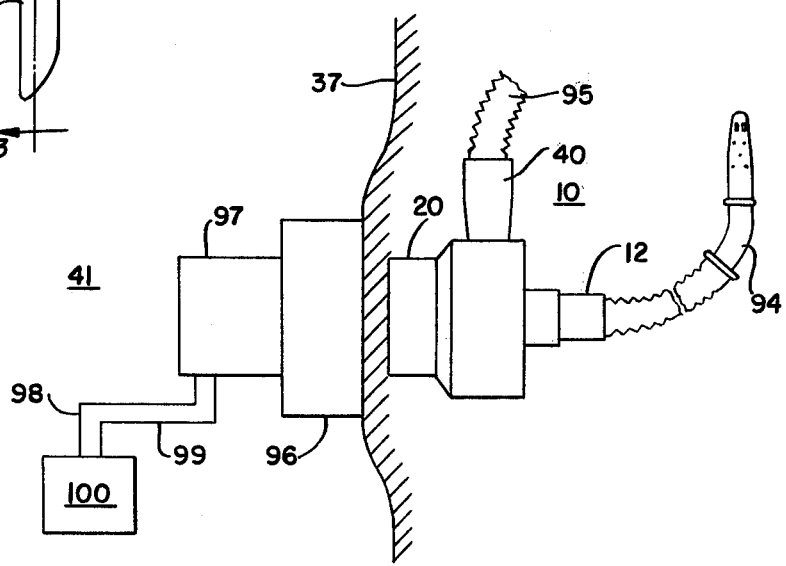
FIG. 6 is a schematic representation showing the pump of the present invention implanted within the human body and coupled through the skin wth an external power unit.

Referring to FIG. 6, there is shown schematically the manner in which the blood pump 10, in a further embodiment of this invention, may be implanted, for example in the chest cavity of a patient. Blood inflow to the pump is through a cannula 94 into the ventricle cavity to the inlet 12. Outflow is from the diffuser tube 40 through a Dacron graft tube 95 to the descending thoraciac aorta. In this manner, the pump 10 receives and discharges blood which otherwise would pass through the heart, so as to reduce the flow of blood through the heart and reduce the pumping load otherwise put on the heart. Presently, it is contemplated that an implanted blood pump 10, as shown in FIG. 6, would not include the feature of lubricating the rotor by a saline solution directed through the rotor housing 20, as shown in FIG. 1.

As shown in FIG. 6, the pump 10 is implanted with the outside transverse surface of the rotor housing 20 underlying the skin surface 37 and the axis of rotation substantially normal to the skin surface 37. The rotor 26 of the pump 10 is driven from a driven magnet power pack indicated generally at 41. The drive magnet power pack 41 is a high-energy magnet similar to that of the pump rotor 26, and is desirably enclosed in a rotor housing 96 to minimize air drag. The drive magnet power pack 41 is mounted to be rotated by a direct current motor 97 connected by connector wires 98 and 99 to a suitable power source 100, such as a small portable battery pack which is easily carried by the patient. The drive magnet pack 41 is disposed immediately adjacent the skin surface 37 of the user in axial alignment with the pump rotor 26. Alternately, the pump rotor 26 may be driven by setting up a rotary electromagnetic field by means of suitable coils disposed adjacent the skin surface in alignment with the pump.

In use, blood is slightly accelerated as it passes through the throat 38 into the scroll impeller chamber 18. The blood is pumped centrifugally by action of the impeller blades 76 rotated at high speeds. The inverted venturi exit from the scroll chamber 18 decelerates the blood flow before it returns through the outlet 14.

In a preferred embodiment, as now contemplated, the blood pump 10 is disposed extracorporeally of the patient and the blood pump 10 is coupled to a pump drive unit comprising a motor driven magnet, motor drive control electronics, a blood flowmeter and other measuring equipment displays and controls. The pump 10 is positioned so that the motor driven magnetic field couples with the magnetic rotor. The pump drive unit and the extracorporeal operation of the pump is further described in the paper entitled *"Twenty-Four Hour Left Ventricular Bypass with a Centrifugal Blood Pump"*, E. F. Bernstein et al, ANNALS of SURGERY, Vol. 181, No. 4. April, 1975, by J. B. Lippincott Company.

Where pulsatile blood flow is considered to be desirable or necessary, the pump output pressure can be made to simulate the pressure pulsation of the natural heart by changing speeds so as to cause the output pressure to change. The rotational velocity of the impeller 24 determines the output pressure.

The pump is optimized in dimension for the blood pressure head and flow rates needed, for example about 100mm Hg pressure and 6 liters/min. flow. By way of reference, the outside diameter of the pump housing is approximately 2 inches. The characteristics of the pump are such that the blood pressure can be established by manipulating the pump impeller rotational velocity only. The pressure curve is flat to within 10% over the range of blood flow needed by the body. Typically, the impeller of the pump is rotated at about 4000 It runs at a constant speed which may be changed, depending upon needs of the situation. The implanted pump has but a single moving configured assembly, namely the impeller 24 connected to rotor 26. The bearing surfaces are lubricated with saline solution. So long as the pump is properly constructed from appropriate material to prevent chemical attack, the pump has an indefinite lifetime. There is no wear on the rotor due to wall contact as a result of the saline lubricant. The external drive motor and magnet can be serviced or quickly replaced without surgery.

Numerous changes may be made in te above-described apparatus and the different embodiments of the invention may be made without departing from the spirit thereof; therefore, it is intended that all matter contained in the foregoing description and in the accompanying drawings shall be interpreted as illustrative and not in a limiting sense.

What is claimed is:

1. A centrifugal blood pump comprising:
   (a) pump housing means having a first chamber, a second chamber and baffle means disposed therebetween and having an aperture communicating between said first and second chamber including an inlet and an outlet for receiving and dispensing blood into and from said first chamber respectively;
   (b) rotor means rotatively mounted within said second chamber and adapted to be rotated by drive means coupled thereto;
   (c) an impeller rotatively disposed within said first chamber and connected by coupling means to said rotor means through said aperture of said baffle plate to be rotated thereby, said impeller including a plurality of blades extending from an axis thereof, whereby blood is pumpled from said inlet to said outlet;
   (d) seal means disposed between said coupling means and said aperture for isolating a lubricating solution disposed within said second chamber from the blood pumped through the first chamber; and
   (e) said impeller includes a hub having a shank end connected via a shank to said impeller, and a conical end, said plurality of blades extending from said hub, each of said plurality of blades having an edge extending from a point disposed relatively close to said baffle plate and adjacent to said shank along a countour corresponding to that of said baffle plate, said shank end of said hub configured to extend from said adjacent points and increasingly away from said baffle plate to thereby define a portion of each of said plurality of blades disposed between said shank end of said hub and said baffle plate for rapidly moving the blood in the vicinity of said shank.

2. A centrifugal blood pump as claimed in claim 1, wherein said hub includes an outer circumference and each of said plurality of blades extends from said hub along a line disposed generally tangential with said outer circumference.

3. A centrifugal blood pump comprising:
   a) a cylindrical pump housing having a scroll pump chamber within said housing, a rotor housing connected to said pump housing having a rotor chamber and a baffle plate separating said pump housing from said rotor housing, an axially disposed aperture in said baffle plate, an impeller having a first shank and disposed in said pump housing;

b) a rotor having a second shank and disposed in said rotor housing, said impeller being connected to said rotor by passing said first shank through said axially disposed aperture in said baffle plate and connected to said second shank;

c) a seal surrounding said first shank and affixed in said axially disposed aperture of said baffle plate to prevent blood in said pump chamber from seeping into said rotor chamber;

d) an axially disposed first inlet in said pump housing for bringing blood into said pump chamber;

e) a transverse first outlet in said pump housing for removing blood from said pump chamber;

f) a second inlet in said rotor chamber for bringing a saline solution lubricant into said rotor chamber; and g) a second outlet in said rotor chamber for removing the saline solution lubricant from said rotor chamber.

4. A centrfugal blood pump as claimed in claim 3, wherein said impeller includes a hub having a shank end connected to said shank and a conical end, and a plurality of radiating blades extending from said hub, said blades being generated from said shank, said hub being maintained at a position out of contact with said baffle plate, whereby said blades direct rapidly the blood from between said shank end of said hub and baffle plate.

5. A centrifugal blood pump as claimed in claim 4, wherein said impeller blades are positioned on said impeller hub such that said blades are offset of the axial center line of said hub, and said impeller hub includes a radius of curvature in the direction of rotation of said impeller.

6. A centrifugal blood pump as claimed in claim 4, wherein said conical end of said hub is axially disposed of said cylindrical pump housing and in-line with said first inlet to deflect incoming blood to said impeller blades.

7. A centrifugal blood pump as claimed in claim 5, wherein said baffle plate separating said pump chamber from said rotor chamber is fluid sealed to prevent passage of fluids between said pump chamber and said rotor chamber.

8. A centrifugal blood pump as claimed in cliam 7, wherein said baffle plate includes a pump chamber surface and a rotor chamber surface, and said seal includes a lip which extends through said baffle plate to said pump chamber surface and is disposed flush with said pump chamber surface.

9. A centrifugal blood pump as claimed in claim 3, wherein there is included means for directing the saline solution into said rotor chamber through said second inlet and from said rotor chamber through said second outlet so that the pressure of that saline solution as exerted against said seal is greater than the pressure exerted upon said seal by the blood in said pump chamber.

10. A centrifugal blood pump as claimed in claim 4, wherein said rotor in said rotor chamber includes a magnet and is driven by a magnetic coupling by motor means disposed exterior to said pump.

11. A centrifugal blood pump as claimed in claim 10 wherein said rotor is lubricated by a saline solution, whereby said rotor is maintained in a friction reduced relationship to said rotor housing.

12. A centrifugal blood pump as claimed in claim 11 wherein said rotor housing includes a thrust plate between said rotor housing and said rotor and said rotor is spaced from said baffle plate by a spacer element which includes an axially disposed aperture for receiving therethrough said second shank on said rotor.

13. A centrifugal blood pump comprising:

a housing;

a scroll pump chamber within said housing;

an axial inlet to and tangential outlet from said scroll pump chamber;

pump means within said scroll pump chamber for moving blood therethrough comprising an impeller mounted for rotation in said chamber;

magnetic drive means for driving said pumping means;

a rotor chamber within said housing for enclosing said drive means and for receiving a liquid lubricant; and at least the portion of said housing enclosing said drive means being electrically non-conductive whereby said drive means may be driven by a mechanically unconnected external source of magnetic energy, wherein an improvement comprising:

a baffle plate disposed between said scroll pump chamber and said rotor chamber and including a center aperture, and said impeller having an impeller shank extending through said center aperture in said baffle plate, said magnetic drive means including a rotor and connected to said impeller shank, a seal disposed in said aperture of said baffle plate to surround said impeller shank and having the property of substantially blocking the passage of the lubricant into said scroll pump chamber, said impeller including a hub from which said shank extends and a plurality of radiating blade members, said hub having a conical end and a shank end, said blade members being secured to the shank end of said hub and said conical end of said hub, said blade members extend from said shank of said hub to maintain said hub out of contact with said baffle plate.

14. A centrifugal blood pump as claimed in claim 13 wherein said blade members being secured to said hub shank end approximate to the point where said shank extends transversely from said hub.

15. A centrifugal blood pump as claimed in claim 14, wherein said blade members are secured offset to said hub at an angle to the axial center line of said hub.

16. A centrifugal blood pump as claimed in claim 15, wherein said rotor housing includes an inlet port and an outlet port for introducing lubricating fluids to said rotor.

17. A centrifugal blood pump as claimed in claim 16, wherein said lubricating fluid is a saline solution.

* * * * *